United States Patent
Galer et al.

(10) Patent No.: US 11,259,958 B2
(45) Date of Patent: Mar. 1, 2022

(54) THERMAL THERAPY DEVICES

(71) Applicant: Stryker Corporation, Kalamazoo, MI (US)

(72) Inventors: James K. Galer, Byron Center, MI (US); Christopher John Hopper, Kalamazoo, MI (US)

(73) Assignee: Stryker Corporation, Kalamazoo, MI (US)

( * ) Notice: Subject to any disclaimer, the term of this patent is extended or adjusted under 35 U.S.C. 154(b) by 644 days.

(21) Appl. No.: 15/675,061

(22) Filed: Aug. 11, 2017

(65) Prior Publication Data

US 2018/0042763 A1  Feb. 15, 2018

Related U.S. Application Data

(60) Provisional application No. 62/373,658, filed on Aug. 11, 2016.

(51) Int. Cl.
*A61F 7/02* (2006.01)
*A61F 7/00* (2006.01)
(Continued)

(52) U.S. Cl.
CPC ............... *A61F 7/02* (2013.01); *A61F 7/007* (2013.01); *A61H 9/0078* (2013.01);
(Continued)

(58) Field of Classification Search
CPC .......... A61F 7/02; A61F 7/007; A61F 7/0085; A61F 7/0097; A61F 2007/0054–0058;
(Continued)

(56) References Cited

U.S. PATENT DOCUMENTS

| | | |
|---|---|---|
| 4,538,311 A | 9/1985 | Hall et al. |
| 4,844,072 A | 7/1989 | French et al. |

(Continued)

FOREIGN PATENT DOCUMENTS

| | | |
|---|---|---|
| CN | 2251310 Y | 4/1997 |
| WO | 2009157856 A1 | 12/2009 |

OTHER PUBLICATIONS

Nerdin, Stacey, "Review: Sleep Number® AirFit Adjustable Pillow with CoolFit Foam", published on The Scenic Life website at www.thesceniclife.com, dated Mar. 9, 2012.

(Continued)

*Primary Examiner* — Tigist S Demie
(74) *Attorney, Agent, or Firm* — Warner Norcross + Judd LLP

(57) ABSTRACT

A thermal pad for controlling a patient's temperature includes first and second chambers defined between interior and exterior layers. The first chamber circulates a temperature controlled fluid from a first inlet to a first outlet. The second chamber is in fluid communication with a port and a plurality of holes defined in the interior layer. Pressurized gas supplied to the second chamber is vented onto the patient to control the microclimate between the patient's skin and the thermal pad. An additional third chamber is provided in some embodiments that urges the thermal pad into contact with the patient when subjected to negative gauge pressure. In other embodiments, a negative gauge pressure chamber is allowed to partially inflate in order to urge the thermal pad into contact with the patient.

20 Claims, 9 Drawing Sheets

(51) Int. Cl.
*A61H 9/00* (2006.01)
*A61B 90/00* (2016.01)
*A61M 13/00* (2006.01)

(52) U.S. Cl.
CPC ....... *A61B 2090/065* (2016.02); *A61F 7/0085* (2013.01); *A61F 7/0097* (2013.01); *A61F 2007/006* (2013.01); *A61F 2007/0054* (2013.01); *A61F 2007/0055* (2013.01); *A61F 2007/0091* (2013.01); *A61F 2007/0239* (2013.01); *A61H 2201/0103* (2013.01); *A61H 2201/0146* (2013.01); *A61H 2201/0207* (2013.01); *A61H 2201/0242* (2013.01); *A61M 13/003* (2013.01)

(58) Field of Classification Search
CPC ........ A61F 2007/006–0068; A61F 2007/0091; A61F 2007/0239; A61H 9/0078; A61H 2201/0103; A61H 2201/0146; A61H 2201/0242; A61H 2201/025; A61H 2201/02–0221; A61B 2090/065; A61M 13/003
See application file for complete search history.

(56) References Cited

U.S. PATENT DOCUMENTS

| | | | | |
|---|---|---|---|---|
| 5,265,293 | A | * | 11/1993 | Spahn .................. A47C 21/046 5/706 |
| 5,437,618 | A | * | 8/1995 | Sikes ........................ A61F 5/34 602/19 |
| 5,482,355 | A | | 1/1996 | Franzen, Jr. |
| 5,486,206 | A | | 1/1996 | Avery |
| 5,948,013 | A | * | 9/1999 | Swezey .................. A47C 7/425 5/636 |
| 5,989,285 | A | * | 11/1999 | DeVilbiss ............ A47C 21/044 607/104 |
| 6,197,045 | B1 | | 3/2001 | Carson |
| 6,245,347 | B1 | | 6/2001 | Zhang et al. |
| 6,371,976 | B1 | | 4/2002 | Vrzalik et al. |
| 6,511,501 | B1 | | 1/2003 | Augustine et al. |
| 6,699,266 | B2 | | 3/2004 | Lachenbruch et al. |
| 6,840,955 | B2 | | 1/2005 | Ein |
| 7,106,662 | B1 | | 9/2006 | Acker, Jr. |
| 7,107,629 | B2 | | 9/2006 | Miros et al. |
| 7,896,910 | B2 | | 3/2011 | Schirrmacher et al. |
| 7,972,287 | B2 | | 7/2011 | Stewart et al. |
| 8,052,624 | B2 | | 11/2011 | Buchanan et al. |
| 8,226,586 | B2 | | 7/2012 | Cazzini et al. |
| 8,460,355 | B2 | | 6/2013 | Cazzini et al. |
| 8,597,217 | B2 | | 12/2013 | Lowe et al. |
| 8,801,272 | B2 | | 8/2014 | Bieberich |
| 8,827,935 | B2 | | 9/2014 | Maxon-Maldonado |
| 9,066,794 | B2 | | 6/2015 | Jusiak et al. |
| 9,119,705 | B2 | | 9/2015 | Parish et al. |
| 9,474,847 | B2 | | 10/2016 | Bonutti et al. |
| 2006/0005314 | A1 | | 1/2006 | Lee |
| 2006/0195168 | A1 | | 8/2006 | Dunbar et al. |
| 2007/0261548 | A1 | * | 11/2007 | Vrzalik ................ A47C 21/044 95/52 |
| 2008/0281297 | A1 | | 11/2008 | Pesach et al. |
| 2009/0005841 | A1 | * | 1/2009 | Schirrmacher ........... A61F 7/02 607/108 |
| 2010/0274331 | A1 | | 10/2010 | Williamson et al. |
| 2011/0077723 | A1 | * | 3/2011 | Parish ........................ A61F 5/34 607/104 |
| 2012/0172774 | A1 | * | 7/2012 | Lowe ........................ A61F 7/02 602/13 |
| 2013/0158443 | A1 | | 6/2013 | Kraal et al. |
| 2014/0200464 | A1 | | 7/2014 | Webster et al. |
| 2014/0200487 | A1 | | 7/2014 | Ramdas et al. |
| 2014/0222121 | A1 | | 8/2014 | Spence et al. |
| 2014/0276257 | A1 | * | 9/2014 | Santa Maria ............. A61F 7/02 601/18 |
| 2015/0366367 | A1 | | 12/2015 | Augustine et al. |
| 2016/0030234 | A1 | | 2/2016 | Lofy et al. |

OTHER PUBLICATIONS

"Z-Flo Positioners by Sundance Enterprises Inc.", available at https://www.medline.com/product/Z-Flo-Positioners-by-Sundance-Enterprises-Inc/Specialty-Positioners/Z05-PF70265?question=z-flo &index=P1&indexCount=1 and available at least as of Aug. 18, 2017.

"Positioning your patients to prevent pressure ulcers," published by Mölnlycke Health Care at http://www.molnlycke.us/turning-and-positioning-system#confirm and available at least as of Aug. 18, 2017.

Otostick News "One Business Woman Versus Prominent Ears", Otostick 2016.

Gaymar Medi-Therm III, Hyper/Hypothermia Machine Ref MTA7912 Service Manual, Nov. 2009.

Altrix Precision Temperature Management System Stryker Operations Manuel, Dec. 2016.

* cited by examiner

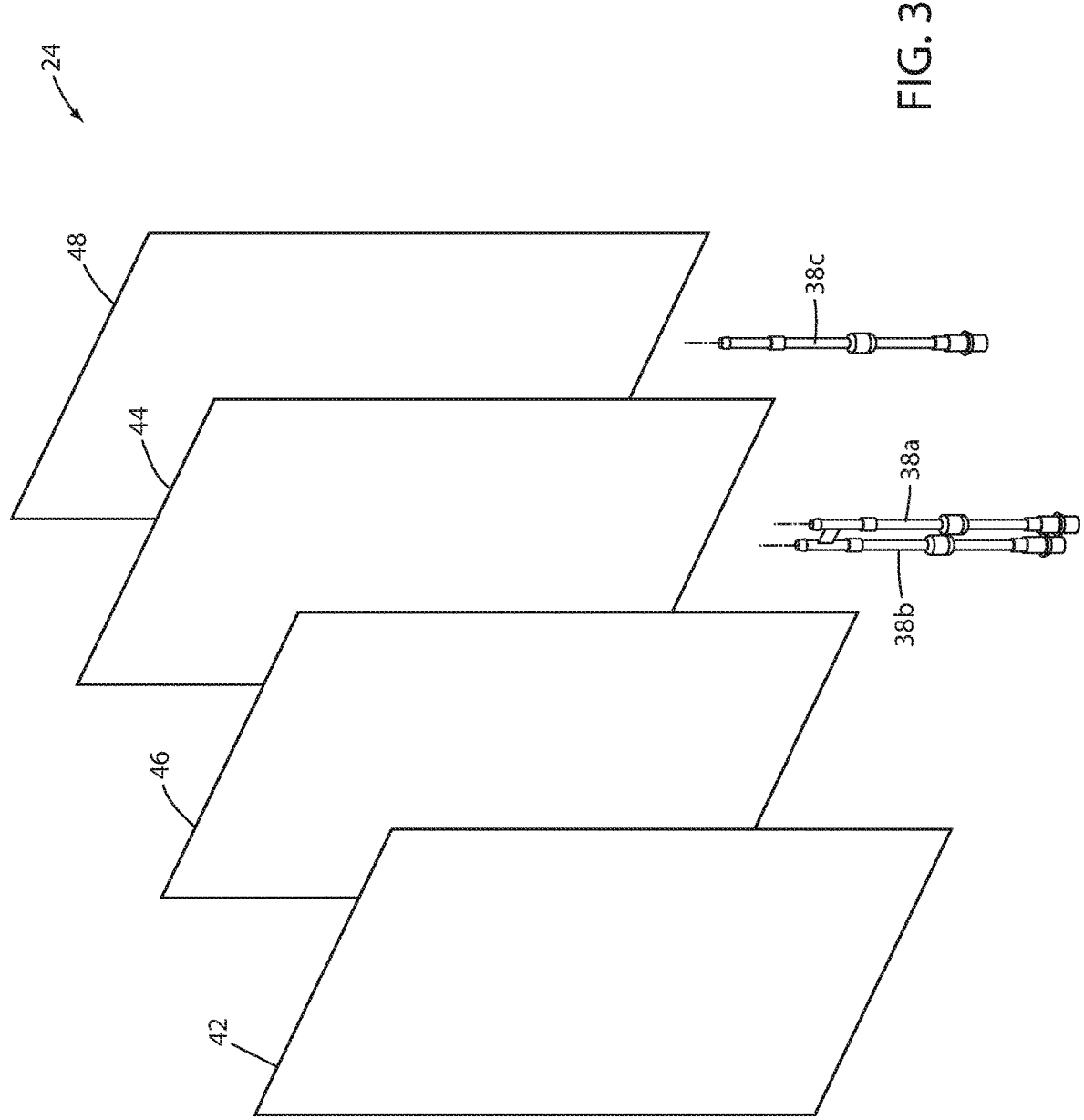

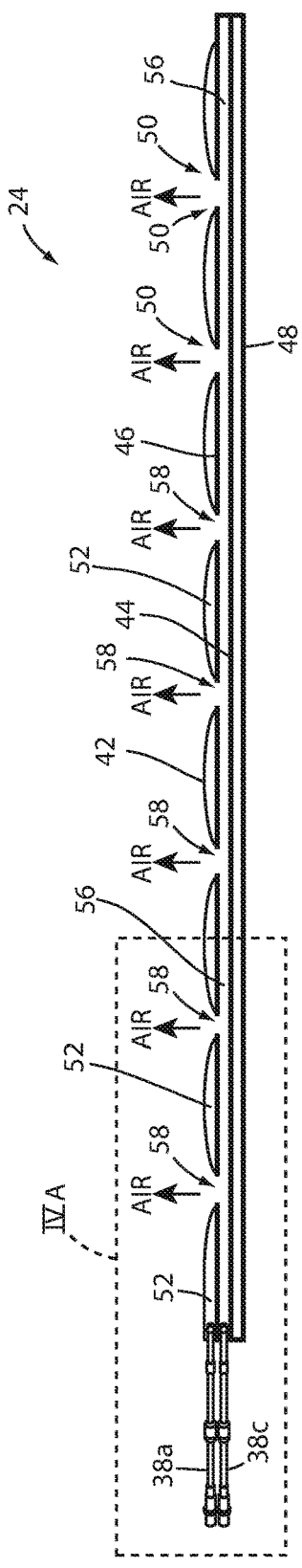
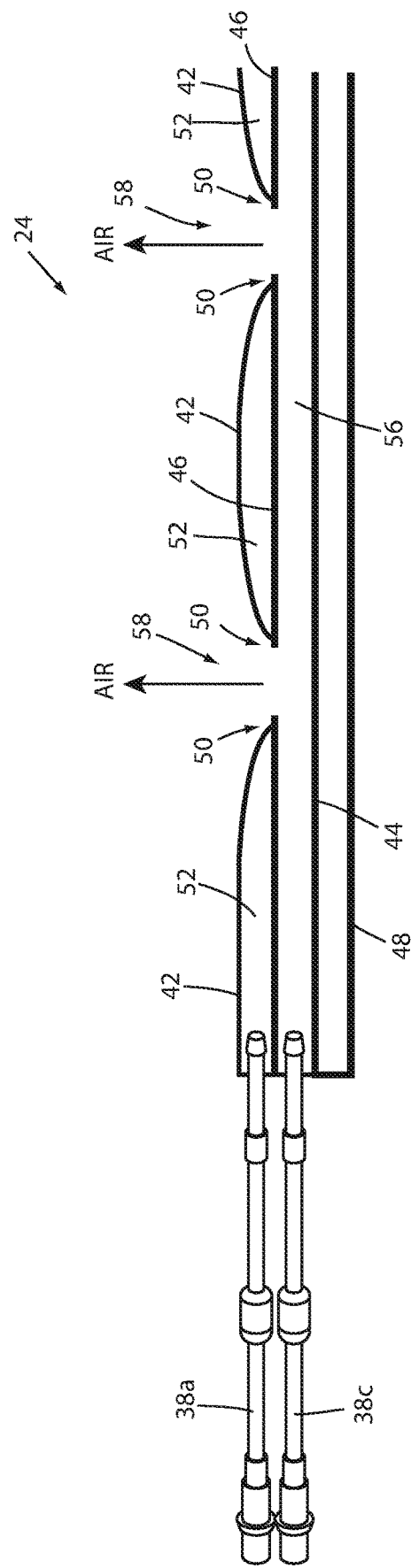

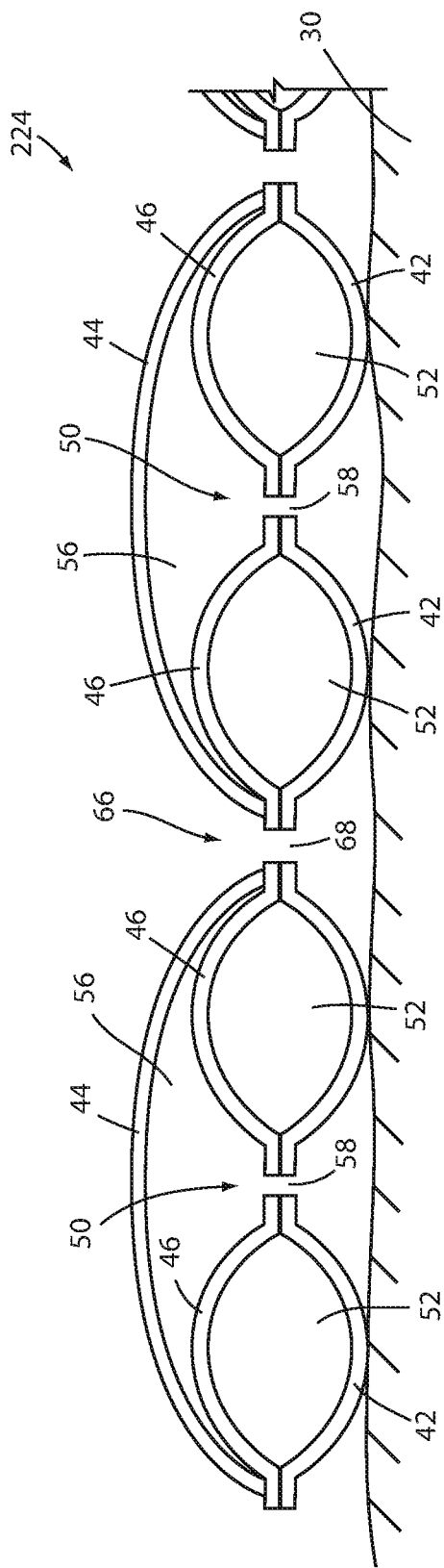
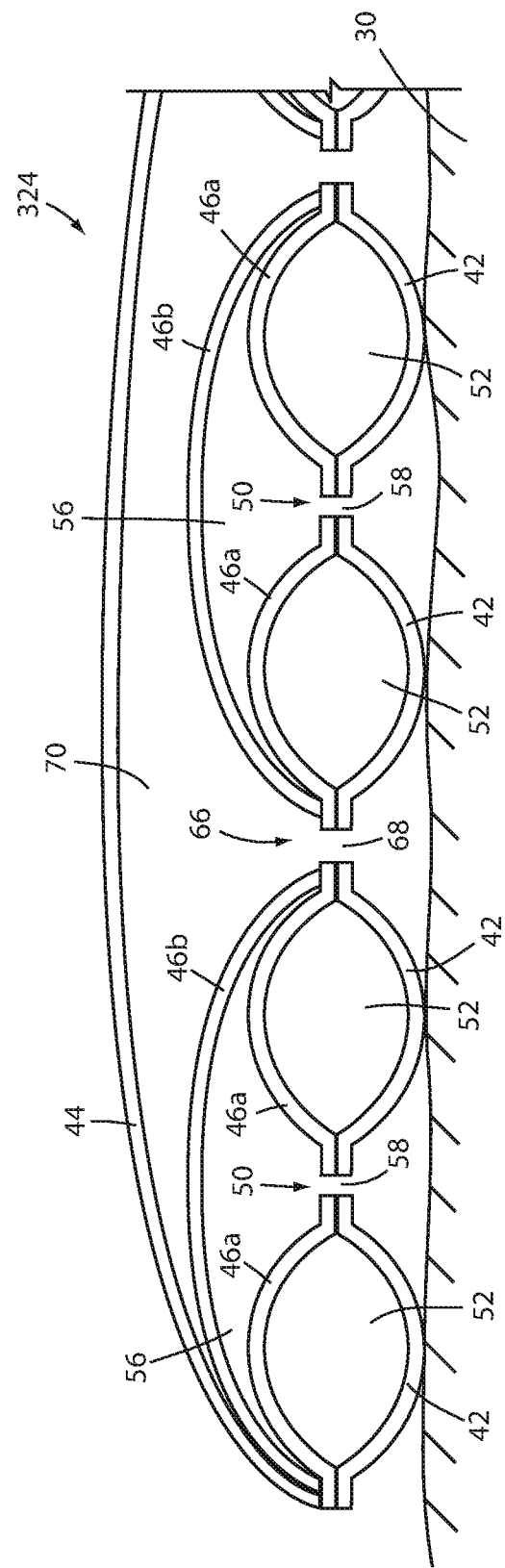
FIG. 9
FIG. 10

THERMAL THERAPY DEVICES

CROSS-REFERENCE TO RELATED APPLICATIONS

This application claims priority to U.S. provisional patent application Ser. No. 62/373,658 filed Aug. 11, 2016, by inventors James Galer et al. and entitled THERMAL THERAPY DEVICES, the complete disclosure of which is incorporated herein by reference.

BACKGROUND

The present disclosure relates to thermal pads that are placed against a patient and receive temperature controlled fluid in order to control a temperature of the patient.

Thermal control systems are known in the art for controlling the temperature of a patient by supplying temperature controlled fluid to one or more thermal pads that are positioned in contact with a patient. The temperature of the fluid is controlled by a thermal control unit that provides temperature controlled fluid to the pad(s). After passing through the pad(s), the fluid is returned to the thermal control unit where any necessary adjustments to the returning fluid temperature are made before being pumped back to the pad(s). In some instances, the temperature of the fluid is controlled to a target temperature, while in other instances the temperature of the fluid is varied as necessary in order to automatically effectuate a target patient temperature.

The pads are placed in close contact with the patient in order to facilitate heat exchange between the patient and the pad. In one common arrangement, three pads are applied to the patient: one applied around the patient's torso, one applied around the patient's right leg, and one applied around the patient's left leg.

SUMMARY

The present disclosure provides various improved aspects to thermal pads that are used as part of a thermal control system. These improved aspects include any one or more of the following features: improved thermal transfer between the pads and the patient; improved microclimate management of the area between the thermal pads and the patient; improved functionality for reducing the risk of deep vein thrombosis developing in the patient; and improved resistance to bacterial growth and/or the development of pressure ulcers in the patient. Other improved aspects of the present disclosure are described in more detail below.

According to one embodiment of the present disclosure, a thermal pad is provided that includes an interior layer, an exterior layer, a liquid chamber, a gas chamber, and a resilient material. The interior layer is adapted to be placed in contact with the patient and the exterior layer faces away from the patient. The liquid chamber is defined between the interior layer and the exterior layer. The liquid chamber is adapted to circulate a temperature controlled fluid from a liquid inlet in fluid communication with the liquid chamber to a liquid outlet in fluid communication with the liquid chamber. The gas chamber is defined between the liquid chamber and the exterior layer and in fluid communication with a sealable port. The gas chamber is hermetically sealed when the sealable port is sealed. The resilient material is positioned inside the gas chamber and adapted to be compressed when a gauge pressure inside the gas chamber is negative and to expand when the sealable port is opened.

According to other aspects, the sealable port includes a user controlled seal for selectively allowing ingress of gas into the gas chamber. The user controlled seal may comprise a threaded cap that selectively engages a threaded cylinder of the sealable port.

The resilient material is a foam material, in some embodiments.

The resilient material comprises a sheet of material having a surface area substantially equal to a length and a width of the gas chamber, in some embodiments.

A strap may be included that is adapted to secure the thermal pad to a patient when the thermal pad is wrapped around a portion of the patient. After the thermal pad is secured around the portion of the patient, an ingress of air into the gas chamber expands the gas chamber and urges the liquid chamber toward the patient.

The thermal pad may be sized to wrap around one of a patient's leg and torso.

The gas chamber is separated from the liquid chamber by a single sheet of flexible material, in some embodiments.

A thermal pad according to another embodiment includes an interior layer, an exterior layer, a first chamber, and a second chamber. The interior layer is adapted to be placed in contact with the patient and the exterior layer faces away from the patient. The first chamber is defined between the interior layer and the exterior layer and is adapted to circulate a temperature controlled fluid from a first inlet in fluid communication with the first chamber to a first outlet in fluid communication with the first chamber. The second chamber is defined between the interior layer and the exterior layer and is in fluid communication with a port and a plurality of holes defined in the interior layer.

According to other aspects, the first chamber is defined between the interior layer and an intermediate layer, and a perimeter of the interior layer is sealed to a perimeter of the intermediate layer. The interior layer and intermediate layer may be secured together at a plurality of internal locations.

Holes are defined at a plurality of the internal locations in some embodiments.

In some embodiments, the intermediate layer and interior layer are secured together at the plurality of internal locations by welds. The holes may be defined in a subset of the welds. In some embodiments, a first set of holes are defined in a first set of the welds and a second set of holes are defined in a second set of the welds wherein the holes of the second set extend through the exterior layer to allow gas inside of said second chamber to be vented to the ambient surroundings.

In some embodiments, the first chamber is a liquid chamber and the second chamber is a gas chamber.

When pressurized gas is delivered to the port in the second chamber, the pressurized gas flows through the holes and onto the patient.

If negative gauge pressure is applied to the port in the second chamber, the negative gauge pressure causes ambient air adjacent the patient's skin to enter the second chamber through the holes. In some embodiments, the holes are distributed with sufficient density over the interior layer such that when negative gauge pressure is applied to the port, suction is created between the interior layer and the patient. The suction urges the thermal pad to retain contact with patient.

In some embodiments, the thermal pad also includes a first intermediate layer, a second intermediate layer, and a third chamber. The first intermediate layer has a perimeter sealed to a perimeter of the interior layer and the first intermediate layer and interior layer are secured together at a plurality of internal locations to define the first chamber therebetween. The second intermediate layer has a perimeter sealed to a perimeter of the exterior layer. The second chamber is defined between the first and second intermediate layers, and the third chamber is defined between the second intermediate layer and the exterior layer.

The third chamber may be adapted to urge the interior layer toward the patient when subjected to a negative gauge pressure, thereby improving thermal contact between the pad and the patient.

In some embodiments, the third chamber is adapted to intermittently urge the interior layer toward the patient when subjected to intermittent negative pressure to help counteract deep vein thrombosis in the patient.

The second and third chambers are in fluid communication with each other through the plurality of holes, in some embodiments.

According to another embodiment, a thermal pad for controlling a patient's temperature is provided that includes an interior layer, an exterior layer, an intermediate layer, a gas chamber, a liquid chamber, and a plurality of interior bonding locations. The interior layer is adapted to be placed in contact with the patient and the exterior layer faces away from the patient. The intermediate layer is positioned between the interior layer and the exterior layer. The gas chamber is defined between the exterior layer and the intermediate layer, and the liquid chamber is defined between the intermediate layer and the interior layer. A first set of the interior bonding locations secures the interior layer to the intermediate layer but not to the exterior layer, and a second set of the interior bonding locations secures the interior layer, the intermediate layer, and the exterior layer together.

In some embodiments, the bonding locations are welds.

A first set of holes may be defined in the first set of the interior bonding locations and a second set of holes may be defined in the second set of the interior bonding locations. The first set of holes allows gas from the gas chamber to exit out of the thermal pad on a side of the thermal pad facing the patient. The second set of holes allows gas positioned between the patient and the thermal pad to pass through the thermal pad and be vented to the ambient surroundings.

In any of the embodiments, one or more insulating layers may be positioned over the exterior layer on a side of the exterior layer opposite the intermediate layer. The insulating layer includes no apertures in some embodiments, while in other embodiments the insulating layer includes a plurality of apertures aligned with the second set of holes.

By applying positive gauge pressure to the port of the gas chamber, the thermal pad exerts pressure against the patient, thereby enabling the thermal pad to be used for reducing a likelihood of deep vein thrombosis.

According to another embodiment, a method of using a thermal pad for controlling a patient's temperature is provided. The method includes drawing air out of a gas chamber defined within the thermal pad until a negative gauge pressure is achieved within the gas chamber. The method further includes hermetically sealing the gas chamber; wrapping the thermal pad around a portion of the patient's body; securing a first end of the thermal pad to a second end of the thermal pad while the thermal pad is wrapped around the portion of the patient's body; and allowing ambient air to return into the gas chamber.

In some embodiments, the method further includes delivering temperature controlled liquid to a liquid chamber defined in the thermal pad. The liquid chamber is fluidly isolated from the gas chamber.

A resilient material within the gas chamber is provided in some embodiments. The resilient material is adapted to be compressed when the negative gauge pressure is achieved within the gas chamber. A cap and threaded port in communication with the gas chamber may be provided. The threaded port creates a hermetic seal for the gas chamber when the cap is secured to the threaded port.

In some embodiments, the step of allowing ambient air to return to the gas chamber includes allowing enough ambient air to return to the gas chamber to cause the gas chamber to urge the liquid chamber toward the portion of the patient's body.

Before the various embodiments disclosed herein are explained in detail, it is to be understood that the claims are not to be limited to the details of operation or to the details of construction, nor to the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

BRIEF DESCRIPTION OF THE DRAWINGS

FIG. 3 is an exploded perspective view of the thermal pad of FIG. 2;

FIG. 4 is a sectional view of the thermal pad of FIG. 2;

FIG. 4A is an enlarged view of the portion of FIG. 4 labeled IVA.

FIG. 9 is a partial sectional view of the thermal pad of FIG. 8; and

FIG. 10 is a partial sectional view of a fourth embodiment of a thermal pad that is usable with the thermal control system of FIG. 1.

DETAILED DESCRIPTION OF THE EMBODIMENTS

Figure 1:
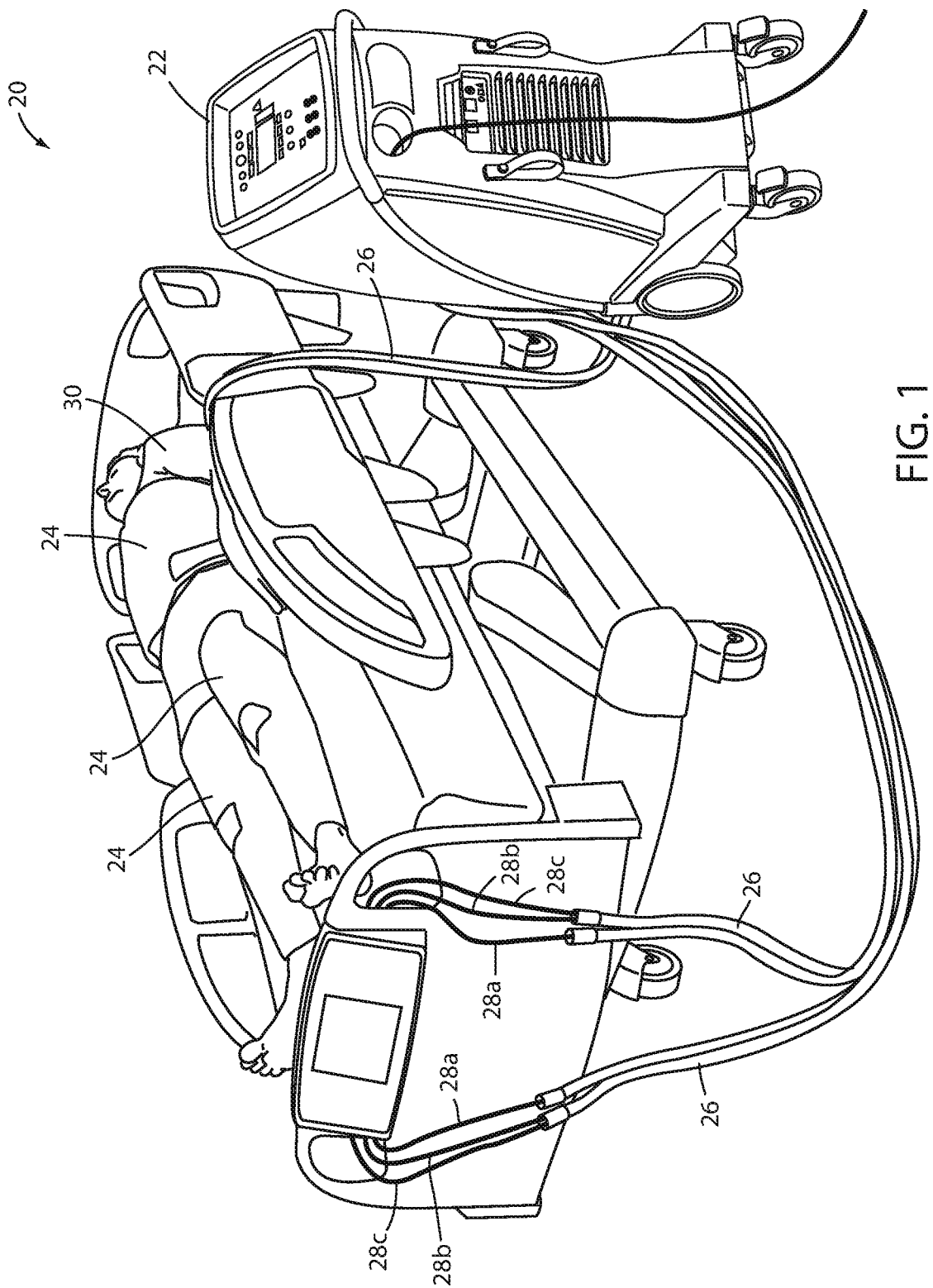
FIG. 1 is a perspective view of an illustrative thermal control system that may be used to provide thermal treatment to a patient.

A thermal control system 20 according to one embodiment of the present disclosure is shown in FIG. 1. Thermal control system 20 is adapted to control the temperature of a patient 30, which may involve raising, lowering, or maintaining the patient's temperature, or combinations thereof. Thermal control system 20 includes a thermal control unit 22 coupled to one or more thermal therapy devices 24. The thermal therapy devices 24 are illustrated in FIG. 1 to be thermal pads, but it will be understood that thermal therapy devices 24 may take on other forms, such as, but not limited to, blankets, vests, patches, caps, or other structure. For purposes of the following written description, thermal therapy devices 24 will be referred to as thermal pads 24, but it will be understood by those skilled in the art that this terminology is used merely for convenience and that the phrase "thermal pad" is intended to cover all of the different variations of thermal therapy devices 24 mentioned above (e.g. blankets, vests, patches, caps, etc.).

Thermal control unit 22 is coupled to thermal pads 24 via a plurality of hoses 26. Each hose includes one or more fluid lines 28. In the embodiment shown in FIG. 1, each hose 26 includes a fluid supply line 28a, a fluid return line 28b, and an auxiliary fluid line 28c. Thermal control unit 22 delivers temperature controlled fluid (such as, but not limited to, water) to the thermal pads 24 via a plurality of supply lines 26a. After the temperature controlled fluid has passed through thermal pads 24, thermal control unit 22 receives the temperature controlled fluid back from thermal pads 24 via a plurality of return lines 26b. Auxiliary lines 28c are used by thermal control unit 22 in different manners, depending upon the capabilities of thermal control unit 22, the construction of one or more of the thermal pads 24, and/or the desired treatment to be applied to the patient 30. As will be discussed in greater detail below, in some instances thermal control unit 22 delivers a pressurized gas (such as, but not limited to, air) to thermal pads 24 via auxiliary line 28c. In other instances, thermal control unit 22 generates negative gauge pressure inside of auxiliary lines 28c such that gas inside of one or more chambers of the thermal pads 24, or within the ambient surroundings of the thermal pads 24, is drawn back into thermal control unit 22. In still other instances, thermal control unit 22 uses auxiliary lines 28c to deliver or receive a liquid. Still other uses are discussed below.

In the embodiment of thermal control system 20 shown in FIG. 1, three thermal pads 24 are used in the treatment of patient 30. A first thermal pad 24 is wrapped around a patient's torso, while second and third thermal pads 24 are wrapped, respectively, around the patient's right and left legs. Other configurations can be used and different numbers of thermal pads 24 may be used with thermal control unit 22, depending upon the number of inlet and outlet ports that are included with thermal control unit 22. By controlling the temperature of the fluid delivered to thermal pads 24 via supply lines 28a, the temperature of the patient 30 can be controlled via the close contact of the pads 24 with the patient 30 and the resultant heat transfer therebetween.

Thermal control unit 22 is adapted to raise or lower the temperature of the fluid supplied to thermal pads 24 via supply lines 28a. Thermal control unit 22 therefore includes a pump and one or more heat exchangers for controlling the temperature of the fluid circulating between thermal control unit 22 and the thermal pads 24. Thermal control unit 22 also includes control structures for controlling the gas gauge pressure of auxiliary lines 28c (negative or positive) and/or structures for using auxiliary line 28c to receive or deliver liquid. The construction of thermal control unit 22 may generally take on a variety of different forms to accomplish these tasks. In some embodiments, thermal control unit 22 is constructed in any of the manners disclosed in following commonly assigned patent applications, as modified to enable the thermal control unit 22 to utilize auxiliary lines 28c to carry out one or more of the functions described in more detail below: U.S. patent application Ser. No. 14/282,383 filed May 20, 2014, by inventors Christopher Hopper et al. and entitled THERMAL CONTROL SYSTEM; U.S. patent application Ser. No. 62/361,124 filed Jul. 12, 2016, by inventor Gregory Taylor and entitled THERMAL CONTROL SYSTEM; and/or U.S. patent application Ser. No. 62/311,054 filed Mar. 21, 2016, by inventor Gregory Taylor and entitled MOBILE THERMAL SYSTEM. The complete disclosures of all of these applications are hereby incorporated herein in their entirety by reference.

Figure 2:
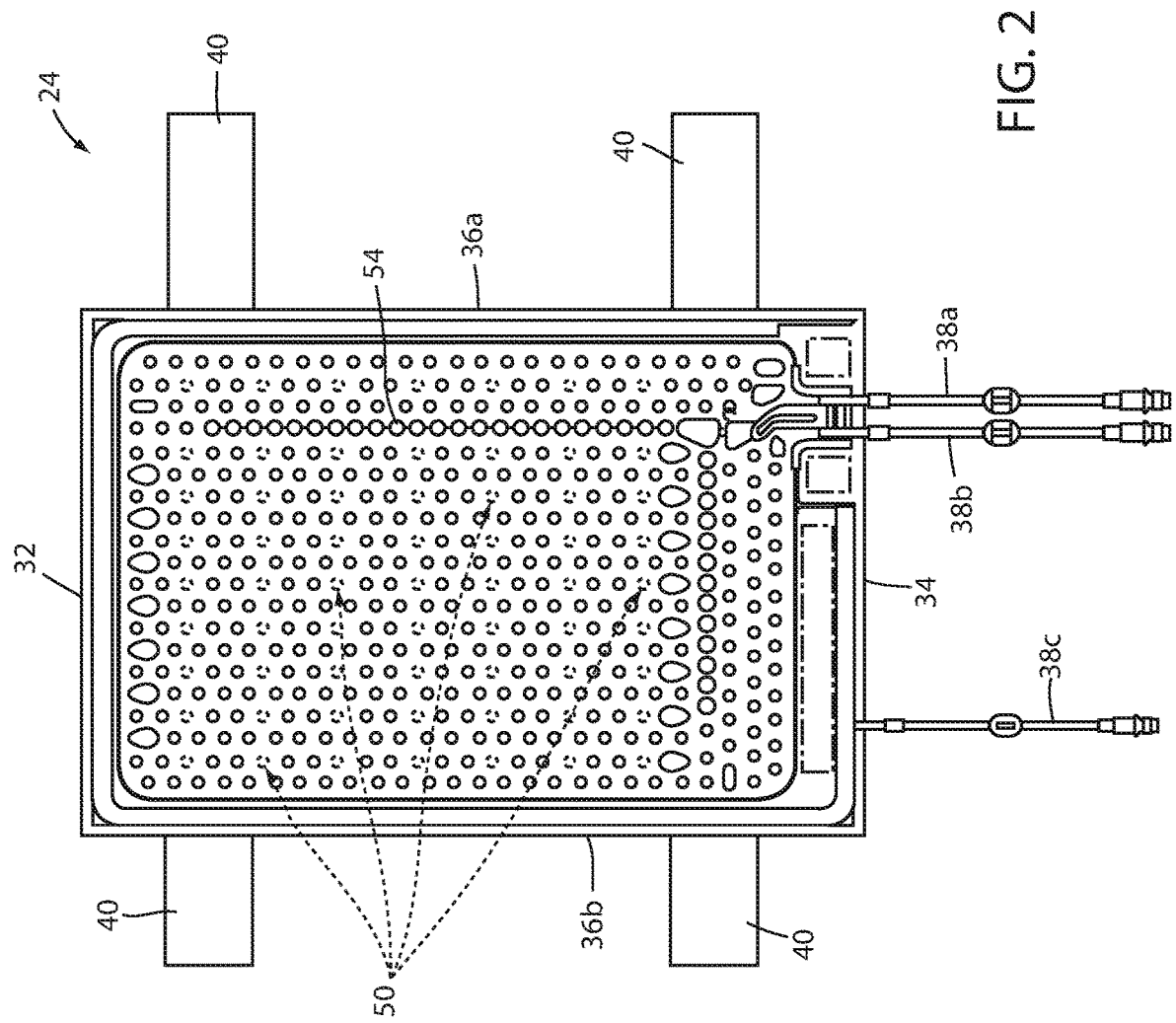
FIG. 2 is plan view of a first embodiment of a thermal pad usable with the thermal control system of FIG. 1.

FIG. 2 illustrates in greater detail one embodiment of a thermal pad 24 that may be used with the thermal control system 20 of FIG. 1. Thermal pad 24 includes a top 32, a bottom 34, a first side 36a and a second side 36 that collectively define a perimeter of thermal pad 24. Thermal pad 24 also includes a fluid inlet hose 38a, a fluid outlet hose 38b, and an auxiliary hose 38c. Fluid inlet hose 38a is adapted to couple to fluid supply line 28a from thermal control unit 22. Fluid outlet hose 38b is adapted to couple to fluid return line 28b from thermal control unit 22. And auxiliary hose 38c is adapted to couple to auxiliary line 28c from thermal control unit 22.

Thermal pad 24 also includes one or more straps 40 that are used to secure thermal pad 24 to patient 30 when in use. Each strap 40 is adapted to releasably attach to another strap 40 after thermal pad 24 has been wrapped around the patient 30. In some embodiments, straps 40 include hook and loop type fasteners, such as those sold under the tradename Velcro. In other embodiments, straps 40 include other types of fasteners for securing themselves to each other in order to maintain pad 24 in a wrapped stated around the patient's leg or torso, such as, but not limited to, tape and/or other repositionable fasteners. In still other embodiments, one or more straps 40 are omitted. In some embodiments where straps 40 are omitted, one or more fasteners may be included directly on a portion of an interior side of interior layer 42 and/or on a portion of an exterior side of exterior layer 44 or insulating layer 48. Still other manners of securing the pad 24 to the patient are possible.

Although thermal pad 24 of FIG. 2 is shown as having a generally rectangular shape, it will be understood by those skilled in the art that this may be varied greatly. That is, thermal pad 24 may take on any shape that is conducive to being wrapped around one or more portions of patient 30. In some embodiments, those thermal pads 24 that are intended to be wrapped around the patient's torso have a different shape than those intended to be wrapped around the patient's legs. Those adapted to be wrapped around the patient's legs may include one or more cutouts or contours that allow the patient to bend his or her knees while thermal pads 24 are wrapped around his or her legs.

FIGS. 3, 4, and 4A illustrate in greater detail the internal construction of thermal pad 24 of FIG. 2. As shown more clearly in FIG. 3, thermal pad 24 includes an interior layer 42, an exterior layer 44, an intermediate layer 46, and an insulating layer 48. Interior layer 42 is designed to face toward the patient 30 while exterior layer 44 is designed to face away from the patient 30. Interior layer 42, intermediate layer 46, and exterior layer 44 are all bonded to each other around their perimeters. Insulating layer 48 is bonded to exterior layer 44 over substantially the entire exterior surface of exterior layer 44. Interior layer 42, exterior layer 44, and intermediate layer 46 may all be constructed from any suitable plastic material that is flexible enough to conform to the patient's body and that provides good thermal conductivity. In some embodiments, interior layer 42, exterior layer 44, and intermediate layer 46 are constructed from a polyester and/or nylon composite. Other materials, however, may be used. Insulating layer 48 is constructed from any suitably flexible material that has relatively poor thermal conductivity properties so as to thermally insulate the other layers (and the fluids contained therein) from the temperature of the ambient surroundings. In some embodiments, insulating layer 48 is constructed from material that includes a polyester foam, or other type of foam. The foam layer may have different sized thicknesses. Still other constructions are possible.

The bonding of interior layer 42, exterior layer 44, and intermediate layers 46 to each other about their periphery may be accomplished in any suitable manner. In some embodiments, the bonding is carried out using welds. Such welds may be implemented via heat welding, ultrasonic welding, Radio Frequency (RF) welding, or by other types of welding.

In addition to being bonded to each other around their perimeters, interior layer 42 and intermediate layer 46 are bonded to each other at a plurality of internal locations 50 (FIGS. 2-4A). The space between interior layer 42 and intermediate layer 46 where they are not bonded to each other defines a first fluid chamber 52. As shown in FIG. 2, in most regions of thermal pad 24, locations 50 are spaced apart from each other. However, in some regions, multiple ones of the locations 50 are contiguous with each other to create walls 54 within first chamber 52 and thereby define fluid paths within thermal pad 24.

In the embodiment illustrated in FIGS. 2-4A, intermediate layer 46 is bonded to exterior layer 44 about its perimeter such that a second fluid chamber 56 is defined inside this perimeter between exterior layer 44 and intermediate layer 46 (see FIGS. 4 and 4A). In some embodiments, intermediate layer 46 may also be bonded to exterior layer 44 at one or more internal locations within their respective perimeters. Second fluid chamber 56 is not hermetically sealed in the embodiment shown in FIGS. 2-4A. Instead, second fluid chamber 56 includes a plurality of vent holes 58 that are in fluid communication with the ambient surroundings of thermal pad 24. In the illustrated embodiment, vent holes 58 are positioned coincident with locations 50. Interior layer 42 and intermediate layer 46 are welded to each other at locations 50 and vent holes 58 are defined in the interior of these welds. In other embodiments, vent holes 58 are can be defined in other locations. Still further, although FIGS. 4 and 4A illustrate a vent hole 58 defined at every location 50 where interior layer 42 and intermediate layer 46 are bonded together, it will be understood that this construction may be varied. That is, in some embodiments, vent holes 58 are only defined in a subset of the locations 50 such that some locations 50 where interior layer 42 and intermediate layer 46 are bonded together do not include vent holes 58 while other ones do include vent holes 58. Still other variations are possible.

The size of vent holes 58 may vary depending upon the construction of thermal pad 24 and the manner in which thermal pad 24 is intended to utilize vent holes 58. In general, however, vent holes 58 are sized such that a pressure differential can be maintained between second chamber 56 and the ambient surroundings (either a negative gauge pressure or a positive gauge pressure, depending upon application).

In one embodiment, thermal pad 24 is adapted to utilize vent holes 58 in order to deliver gas (or a gas/fluid mixture in some embodiments) supplied from thermal control unit 22 to the patient's skin. In such embodiments, the particular gas may be varied. For example, in one such embodiment, thermal control unit 22 delivers pressurized air to auxiliary line 28c and auxiliary hose 38c, which supplies second chamber 56 with a supply of pressurized air. The pressurized air leaks out of vent holes 58 where it comes into contact with the patient. The pressurized air may be temperature and/or humidity controlled, or it may have its temperature and/or humidity uncontrolled. By supplying pressurized air to second chamber 56 and venting it toward the skin of the patient, moisture between the patient and the thermal pad 24 can be better controlled. For example, the pressurized air can be used to evaporate condensation, sweat, and/or other liquids on the patient's skin so as to maintain a relatively dry microclimate between the patient's skin and the thermal pad 24. This dry environment helps stop or retard the growth of bacteria in this microclimate. The dry environment may also help prevent or alleviate skin breakdown or damage, including, but not limited to, pressure ulcers.

In some embodiments of thermal control unit 22, thermal control unit 22 is adapted to deliver pressurized air to second fluid chamber 56 that has its humidity controlled such that the microclimate between the patient's skin and thermal pad 24 is maintained at a level that is neither too dry nor too moist. Alternatively, or additionally, thermal control unit 22 is configured in some embodiments to deliver pressurized air to second fluid chamber 56 that includes one or more medicated vapors. The medicated vapors include medication that is designed to prevent or treat one or more conditions relating to the patient's skin.

Thermal control unit 22 is configurable with respect to the timing and pressure of the pressurized gas that is delivered to second fluid chamber 56. In some embodiments of thermal control unit 22, the pressurized gas is delivered intermittently at time intervals that are configurable by the user. In other embodiments, the pressurized gas is delivered continuously, resulting in a steady stream of air loss from second fluid chamber 56 as the pressurized gas exits through vent holes 58 and is directed into contact with the patient's skin. In still other embodiments, combinations of continuous and intermittent applications of pressurized gas may be generated by thermal control unit 22, including applications that have different pressure levels.

In some embodiments, thermal pad 24 may be used to apply intermittent pneumatic compression to the patient by oscillating the pressure of fluid delivered to second fluid chamber 56. Such compression may help in the prevention and/or treatment of deep vein thrombosis. In order to apply such pressure, thermal pad 24 is first wrapped around a portion of the patient's body and secured thereto by way of straps 40, or other means. After thermal pad 24 is secured to the patient's body portion, pressurized gas is supplied to second fluid chamber 56 at a rate that is faster than the rate at which the gas is vented through vent holes 58. This causes second fluid chamber 56 to inflate, such that the space between exterior layer 44 and intermediate layer 46 increases. This increase in space urges first fluid chamber 52 (which contains the temperature controlled fluid supplied by thermal control unit 22) toward the patient, thereby applying a compressive force to the patient. The compressive force is subsequently relaxed by decreasing the pressure of the fluid supplied to first fluid chamber. Thereafter, the pressure is increased again, and so on, resulting in oscillating pneumatic compressions being applied to the patient.

In order to facilitate the application of pneumatic compression to the patient using thermal pad 24, it may be helpful to couple straps 40 to exterior layer 44 and/or insulating layer 48, and/or to utilize a relatively inelastic material for exterior layer 44 and/or insulating layer 48. Any of these techniques help direct the expansion of second fluid chamber 56 inwardly toward the patient, rather than outwardly and away from the patient. Such inward expansion results in compressive forces being applied to the patient.

Thermal pad 24 may also be used with a thermal control unit 22 that generates negative gauge pressure in auxiliary line 28c (and thus auxiliary hose 38c and second fluid chamber 56). Such negative gauge pressure allows thermal pad 24 to be used to provide at least two different functions. First, the generation of negative gauge pressure in second fluid chamber 56 allows the microclimate between thermal pad 24 and the patient's skin to be controlled. Second, the generation of negative gauge pressure in second fluid chamber 56 allows the thermal pad 24 to apply a suction force to the patient's skin, thereby drawing thermal pad 24 into close contact with the patient's skin and/or maintaining such close contact.

When used to control the microclimate, the air drawn into second fluid chamber 56 travels through auxiliary hose 38c and auxiliary line 28c until it reaches thermal control unit 22. Thermal control unit 22 vents the withdrawn air to the ambient surroundings. By drawing air into second fluid chamber 56 and venting it via thermal control unit 22, thermal pad 24 helps eliminate moisture build up in this microclimate by continuously or intermittently circulating air through it. The air that is continuously or intermittently drawn out of this microclimate is replaced by ambient air that leaks into the microclimate through one or more gaps between the patient's skin and the perimeter of thermal pad that tend to form due to incomplete sealing of the thermal pad 24 to the patient's skin around the entire perimeter of thermal pad 24.

When used to apply suction to the patient, thermal control unit 22 generates a negative gauge pressure inside of second fluid chamber 56 that is large enough to create a suction force between thermal pad 24 and the patient's skin, thereby helping to ensure that thermal pad 24 stays in, or is drawn into, close contact with the patient's skin. This close contact helps improve the efficiency of the thermal transfer between the patient and thermal pad 24. When creating this suction, some local regions of thermal pad 24 will likely adhere to patient with greater forces than other local regions. However, by applying sufficient negative gauge pressure and wrapping thermal pad 24 close enough to the patient's skin, a sufficiently large area of thermal pad 24 can be adhered to the patient to ensure good thermal conductivity between the patient and thermal pad 24. The different levels of localized adherence of thermal pad 24 to the patient result from the fact that some vent holes 58 will likely become effectively sealed by the patient's body contacting the localized region of thermal pad 24 that surrounds those vent holes 58, while other vent holes 58 may not experience such effective sealing by the patient's body. The latter vent holes 58 will continue to draw air into second fluid chamber 56 from the ambient surroundings, while the former vent holes 58 will draw little to no air into second fluid chamber 56.

It will be understood by those skilled in the art from the foregoing description that thermal pad 24 can be used to simultaneously provide both suction and microclimate control when negative gauge pressure is created in second fluid chamber 56. This is provided due to the fact that some vent holes 58 will circulate air out of the microclimate while other vent holes will become effectively plugged by the patient's body, resulting in greater adhesive forces in those regions where vent holes 58 are plugged. As the patient moves, the composition of the plugged and unplugged vent holes 58 will likely vary, thereby ensuring that air flow is provided to all regions of the patient's skin enveloped by thermal pad 24.

Figure 5:
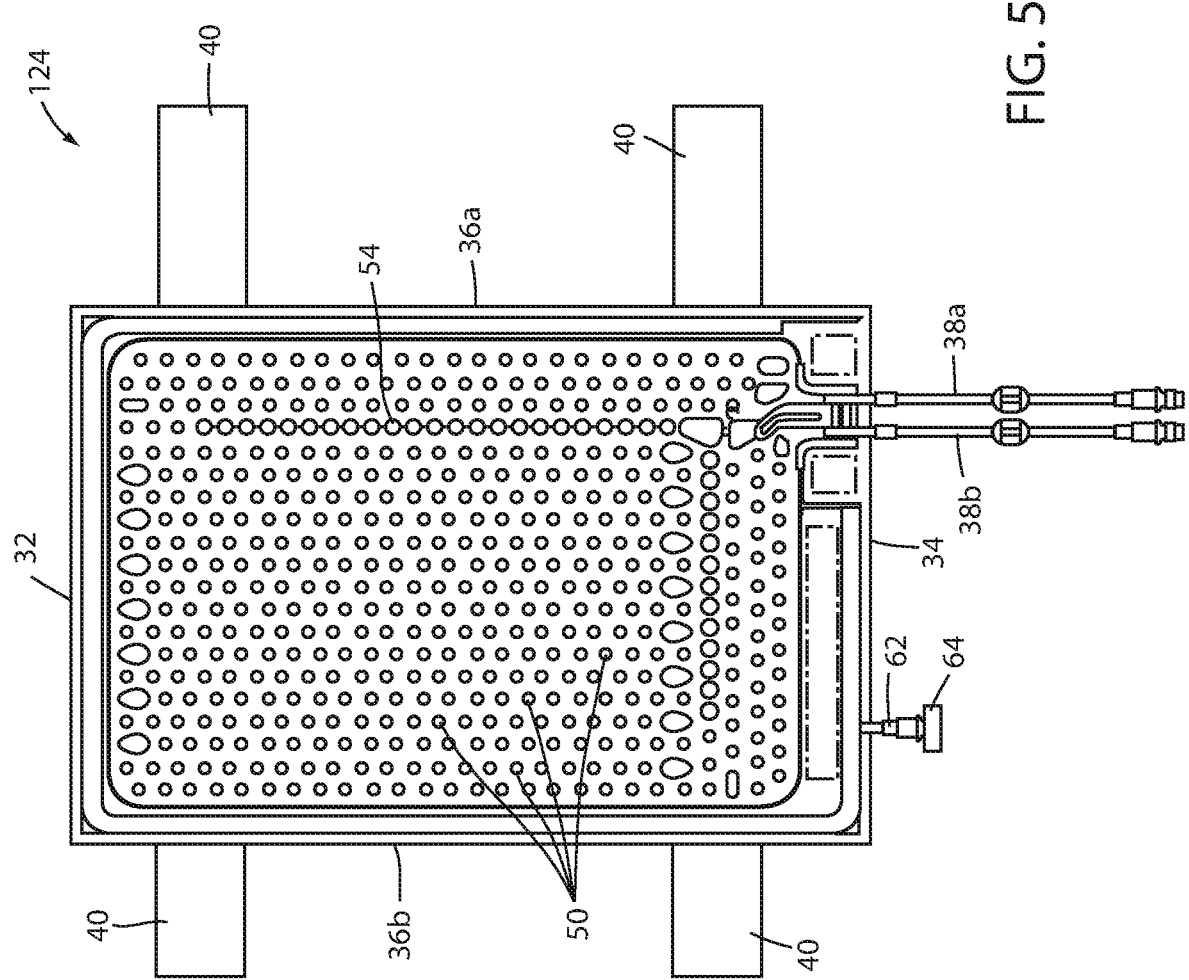
FIG. 5 is a plan view of a second embodiment of a thermal pad usable with the thermal control system of FIG. 1.
Figure 6:
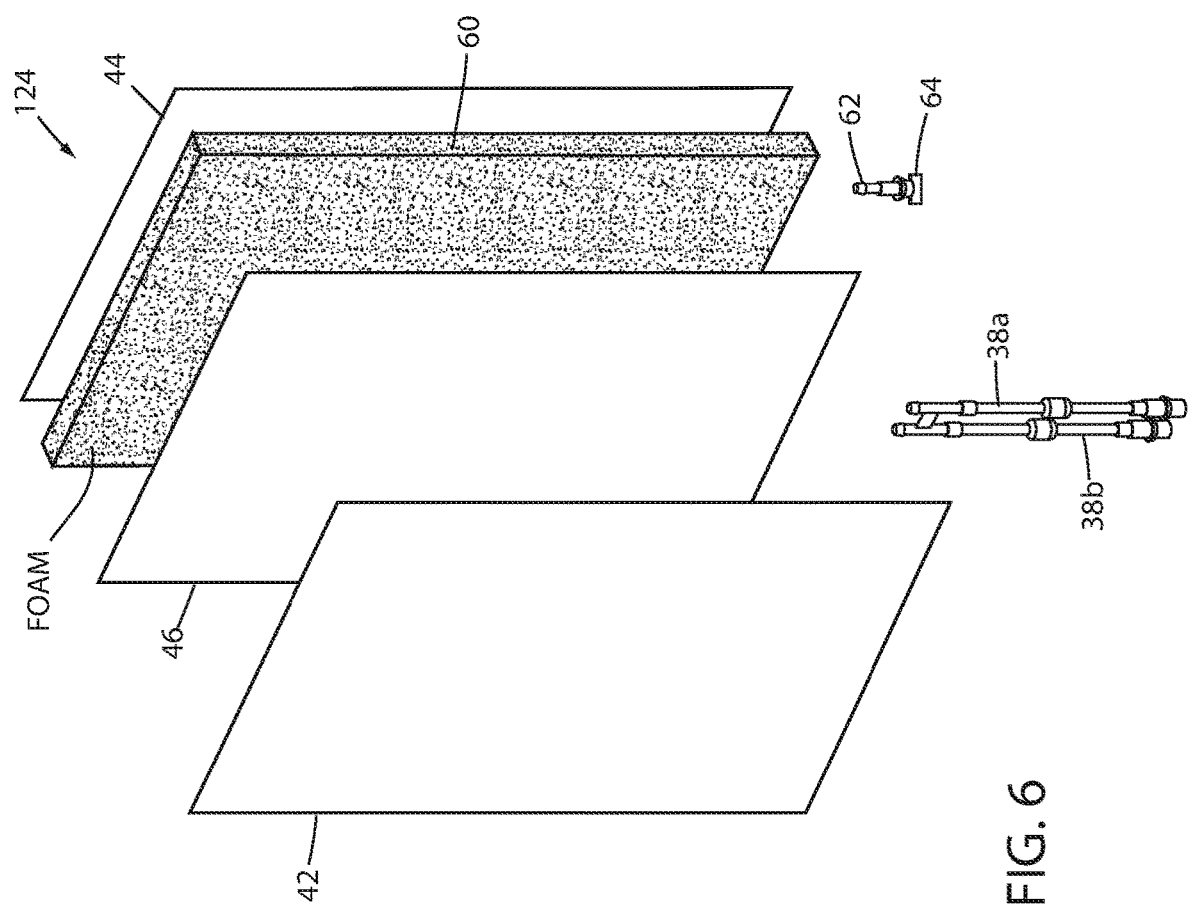
FIG. 6 is an exploded perspective view of the thermal pad of FIG. 5.
Figure 7:
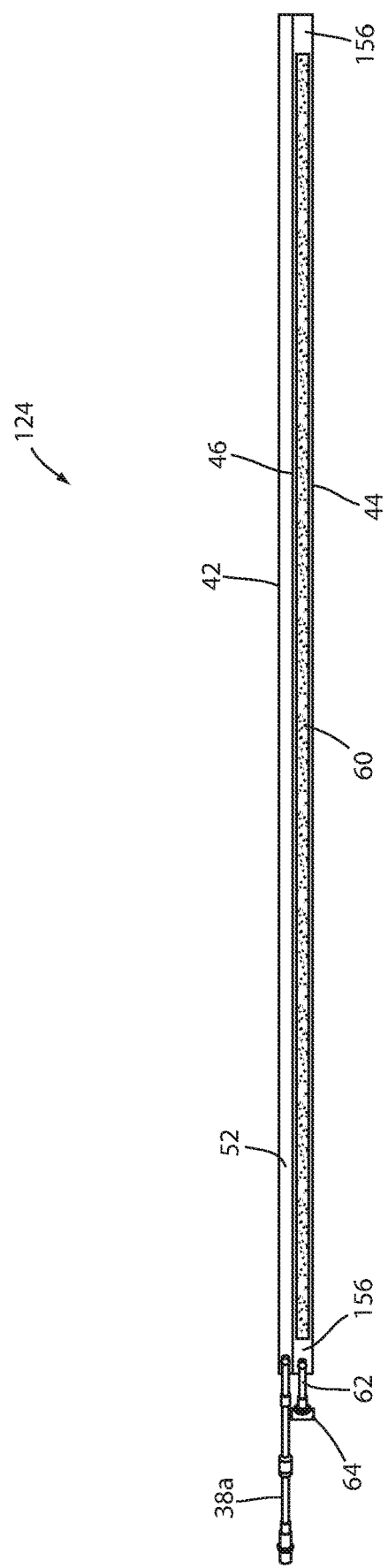
FIG. 7 is a sectional view of the thermal pad of FIG. 5.

FIGS. 5-7 illustrate an alternative embodiment of a thermal pad 124 according to the present disclosure. Thermal pad 124 includes a number of components and/or features that are the same as thermal pad 24. Those components or features that are common are labeled with the same reference numbers used to describe thermal pad 24 and, unless otherwise explicitly stated below, operate in the same manner or provide the same function as previously described. Those components or features that are different from thermal pad 24 are provided with a new reference number and described in more detail below.

Thermal pad 124 includes an interior layer 42, an exterior layer 44, and an intermediate layer 46 (FIG. 6). Interior layer 42 is bonded to intermediate layer 46 around its perimeter in the same manner as interior layer 42 and intermediate layer 46 of thermal pad 24. That is, interior layer 42 is also bonded to intermediate layer 46 at a plurality of internal locations 50 (FIG. 5), and the spaces between interior layer 42 and intermediate layer 46 where they are not bonded to each other define a first fluid chamber 52 in the same manner as thermal pad 24. Further, as with thermal pad 24, multiple ones of the locations 50 may be positioned to be contiguous with each other to create walls 54 within first chamber 52 and thereby define fluid paths within thermal pad 124.

Exterior layer 44 is bonded about its perimeter to intermediate layer 46. In the illustrated embodiment, exterior layer 44 is not bonded to intermediate layer 46 at any interior locations. However, it will be understood that, in some alternative embodiments, exterior layer 44 and intermediate layer 46 may be bonded to each other at one or more interior locations. The interior region between exterior layer 44 and intermediate layer 46 where these two layers are not bonded together defines a second fluid chamber 156. Second fluid chamber 156 is partially or completely filled by a sheet of resilient material 60. In at least one embodiment, resilient material sheet 60 is made from foam, although it will be understood by those skilled in the art that other materials may be used that are capable of performing the functions described below. In the illustrated embodiment, sheet 60 has substantially the same length, width, and shape as exterior layer 44 and intermediate layer 46 so as to substantially fill all of second fluid chamber 156. Resilient sheet 60, however, may be dimensioned differently and, in some embodiments, may be comprised of separate pieces of resilient material.

Second fluid chamber 156 also includes a port 62 having a removable cap 64, or other type of seal. Cap 64, when secured to port 62, hermetically seals second fluid chamber 156 so that substantially no fluid flows into or out of second fluid chamber 156. When cap 64 is removed, or loosened, fluid (such as, but not limited to, air) is allowed to flow into or out of second fluid chamber 156, as discussed below. In some embodiments, cap 64 is threaded and sized to match corresponding threads defined at the end of port 62. In these embodiments, cap 64 may be rotated on port 62 in a first direction (e.g. clockwise) to tighten cap 64 to port 62 and rotated in a second direction (e.g. counterclockwise) to loosen the connection between cap 64 and port 62. Other structures that allow a user to selectively seal and unseal second fluid chamber 156 may alternatively be used.

Thermal pad 124 is adapted to automatically assume a snug fit between the patient's skin and thermal pad 124. However, unlike pad 24 that has positive or negative gauge pressure generated in second fluid chamber 56 in order to keep pad 24 in close contact with the patient (in some embodiments), thermal pad 124 does not achieve its function of assuming a snug fit between the patient's skin and thermal pad 124 by requiring an external device (e.g. thermal control unit 22) to supply a source of air having negative or positive gauge pressure. As discussed in greater detail below, thermal pad 124 achieves this function by allowing a user to selectively control how much ambient air is allowed to enter into second fluid chamber 154 using cap 64.

In at least one embodiment, when thermal pad 124 is first sold to a user, the air inside of second fluid chamber 156 is evacuated so that a vacuum, or near vacuum is created inside of second fluid chamber. During this process, resilient material sheet 60 is compressed so as to be substantially flat. Cap 64, or some other seal, is then applied to port 62 so that no air can enter into second fluid chamber 156. Thermal pad 124 is subsequently maintained in this state (i.e. second fluid chamber 156 is in a vacuum/near vacuum and sheet 60 is compressed) until thermal pad 124 is ready for use.

When thermal pad 124 is ready to be used, thermal pad 124 is wrapped around the patient at the desired location and secured thereto by straps 40. After secured in the desired location, the user twists cap 64 (or otherwise loosens the seal over port 62) so as to allow ambient air into second fluid chamber 156. As the ambient air is allowed to enter into second fluid chamber 156, resilient material sheet 60 expands. Further, this expansion is directed inwardly toward the patient because straps 40 are secured to each other, thereby substantially preventing resilient material sheet 60 from expanding outwardly. The expansion of resilient sheet 60 toward the patient urges thermal pad 124 into closer contact with the patient. Once the desired level of snugness between thermal pad 124 and the patient is achieved, the user re-seals port 62, such as by tightening cap 64 so that a hermetic seal is reformed. In some instances, the user may wish to allow enough air into second fluid chamber 156 such that the air pressure inside of second fluid chamber 156 matches the ambient air pressure. In those instances, the user does not need to reseal port 62 in order to maintain the level of snugness achieved by the expansion of resilient sheet 60.

Once the desired level of snugness is achieved, temperature controlled fluid is delivered to fluid inlet hose 38a of thermal pad 124 and circulates through first fluid chamber 52. The circulating fluid delivers thermal energy to the patient or absorbs thermal energy from the patient, depending upon the temperature of the fluid relative to the temperature of the patient. After passing through first fluid chamber 52, the circulating fluid travels out of pad 124 via outlet hose 38b and returns back to thermal control unit 22.

In some instances, the ability of second chamber 156 and resilient sheet 60 to snugly urge thermal pad 124 into contact with the patient may be restored after use by coupling port 62 to a source of negative gauge pressure and subsequently sealing second fluid chamber 156 after air is drained out of it. One such source of negative gauge pressure is thermal control unit 22 (via auxiliary line 28c). Other sources, however, may be used. Alternatively, thermal pad 124 may be designed so that the automatic patient compression feature of the resilient sheet 60 and the evacuated second fluid chamber 156 may only be used a single time.

The expansion of resilient sheet 60 when ambient air is allowed to enter through port 62 is due to the fact that resilient sheet 60 has uncompressed dimensions that are larger than its dimensions when air is evacuated from second chamber 156. In other words, when port 62 is opened, it is the natural expansion of resilient sheet 60 back toward its uncompressed state that helps draw air into second chamber 156 and expand the size of second chamber 156.

Thermal pad 124 may be modified from the embodiments shown in FIGS. 5-7. For example, although thermal pad 124 is shown in FIGS. 5-7 without a separate insulation layer 48, thermal pad 124 can be modified to include such a layer. When so modified, the insulation layer 48 may be coupled to exterior layer 44. Alternatively, exterior layer 44 may be modified to provide a thermal insulating function in addition to providing half of the structure of second fluid chamber 156.

Still further, thermal pad 124 can be modified to include the structure of thermal pad 24 and/or thermal pad 24 can be modified to include the structure of thermal pad 124. In either case, such a modified embodiment include first fluid chamber 52 for circulating the temperature controlled fluid, second fluid chamber 56 for providing negative or positive gauge to the microclimate between the pad and the patient's skin, and yet another chamber 156 for housing resilient sheet 60. As yet another modification, cap 64 may be dispensed with and port 62 modified to be constructed of an elongated flexible material that can be rolled or folded over on itself to seal second fluid chamber 56 without the use of a cap. Unrolling or unfolding the flexible material allows air into second fluid chamber 56, enabling it to expand. Still other modifications are possible.

Figure 8:
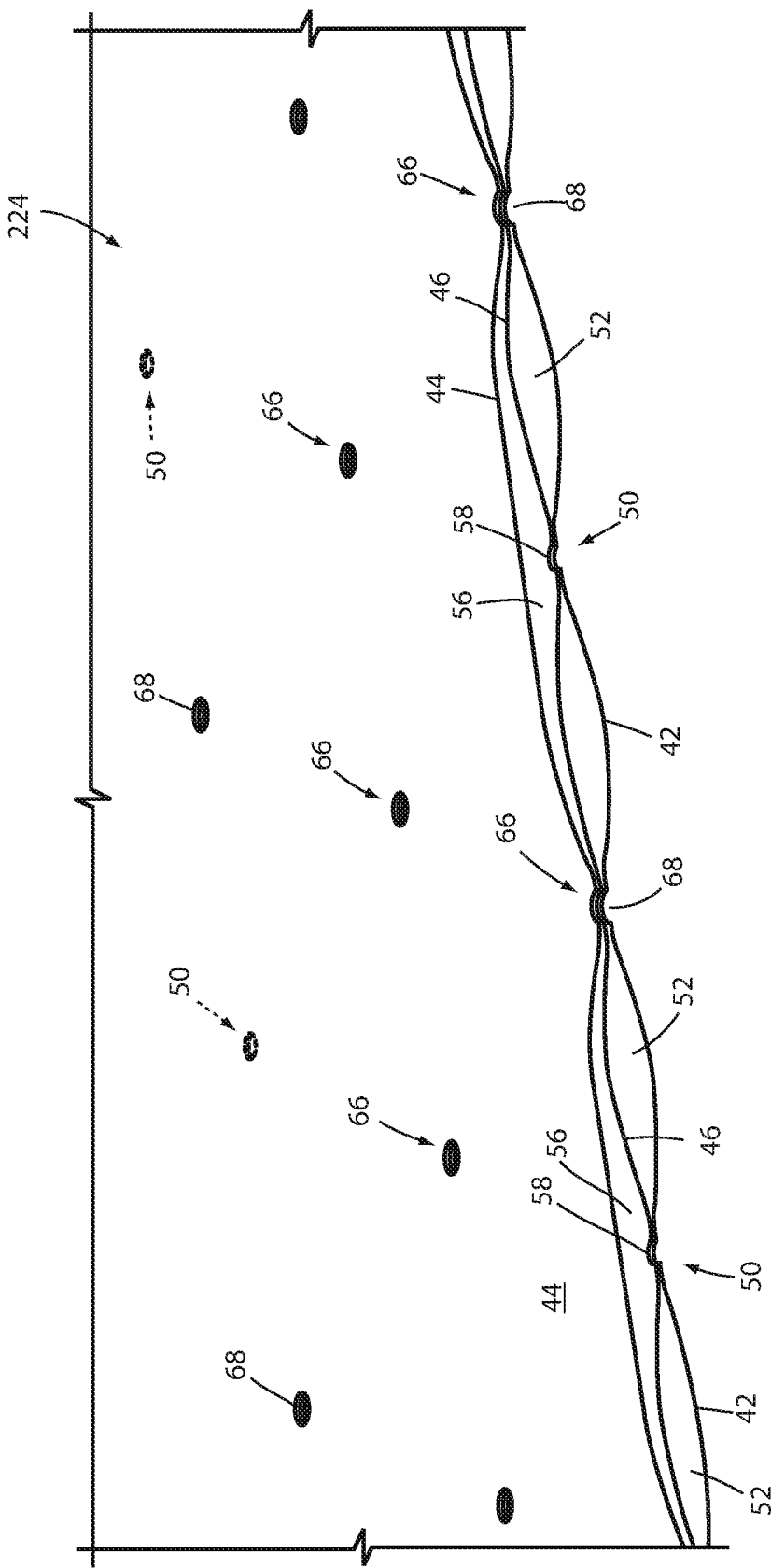
FIG. 8 is a partial sectional perspective view of a third embodiment of a thermal pad that is usable with the thermal control system of FIG. 1.

FIGS. 8 & 9 illustrate a second alternative embodiment of a thermal pad 224 according to the present disclosure. Thermal pad 224 includes a number of components and/or features that are the same as thermal pad 24. Those components or features that are common are labeled with the same reference numbers used to describe thermal pad 24 and, unless otherwise explicitly stated below, operate in the same manner or provide the same function as previously described. Those components or features that are different from thermal pad 24 are provided with a new reference number and described in more detail below.

Thermal pad 224 includes an interior layer 42, an exterior layer 44, and an intermediate layer 46 (FIGS. 8 & 9). Interior layer 42 is bonded to intermediate layer 46 around its perimeter in the same manner as interior layer 42 and intermediate layer 46 are bonded in thermal pad 24. That is, interior layer 42 is also bonded to intermediate layer 46 at a plurality of internal locations 50, and the spaces between interior layer 42 and intermediate layer 46 where they are not bonded to each other define a first fluid chamber 52 in the same manner as thermal pad 24. Intermediate layer 46 is bonded to exterior layer 44 about its perimeter such that a second fluid chamber 56 is defined inside this perimeter between exterior layer 44 and intermediate layer 46. In some embodiments, intermediate layer 46 may also be bonded to exterior layer 44 at one or more internal locations within their respective perimeters. As with thermal pad 24, second fluid chamber 56 of thermal pad 224 is not hermetically sealed, but instead includes a plurality of vent holes 58 that are in fluid communication with the ambient surroundings of thermal pad 224. Vent holes 58 are positioned coincident with locations 50.

Thermal pad 224 differs from thermal pad 24 in that thermal pad 224 includes a plurality of internal bonding locations 66 where all three layers 42, 44, and 46 are bonded together. Further, all or a subset of the bonding locations 66 include vent holes 68 that enable fluid communication between opposite faces of thermal pad 224. That is, vent holes 68 provide openings for fluid that is positioned in the microclimate between thermal pad 224 and the patient's skin to travel to the ambient surroundings of thermal pad 224, and vice versa.

As with thermal pad 24, first fluid chamber 52 includes an inlet hose 38a and an outlet hose 38b (not shown) that couple to supply line 28a and return line 28b, respectively. Hoses 38a and 38b allow temperature controlled fluid to circulate through first fluid chamber 52. Thermal pad 224 also includes an auxiliary hose 38c that couples to auxiliary line 28c of thermal control unit 22. Thermal pad 224 can be used with a thermal control unit 22 that applies positive or negative gauge pressure to auxiliary line 28c, or combinations of the two. When creating positive gauge pressure inside of second fluid chamber 56, thermal pad 224 can be used for applying compressions to the patient and/or for microclimate control in the same manners discussed above with respect to thermal pad 24. When creating negative gauge pressure inside of second fluid chamber 56, thermal pad 224 can be used for creating suction between thermal pad 224 and the patient's skin and/or for controlling the microclimate between thermal pad 224 and the patient's skin. Medicated vapors may also be provided to second fluid chamber 56 by thermal control unit 22 in some embodiments.

Although not illustrated, thermal pad 224 may be modified to include an insulating layer that is coupled to exterior layer 44, or exterior layer 44 may be modified so as to provide thermal insulation between the ambient surroundings and first and second fluid chambers 52 and 56. When a separate insulating layer is applied to exterior layer 44, the insulating layer includes vents holes that are aligned with vent holes 68. Still other modifications to thermal pad 224 are possible, including, but not limited to, the addition of chamber 156 and resilient sheet 60 of thermal pad 124 to thermal pad 224.

FIG. 10 illustrates yet another alternative embodiment of a thermal pad 324 according to the present disclosure. Thermal pad 324 includes a number of components and/or features that are the same as thermal pads 24 and/or 224. Those components or features that are common are labeled with the same reference numbers used to describe thermal pads 24 and 224 and, unless otherwise explicitly stated below, operate in the same manner or provide the same function as previously described. Those components or features that are different from thermal pads 24 and/or 224 are provided with a new reference number and described in more detail below.

Thermal pad 324 includes an interior layer 42, an exterior layer 44, a first intermediate layer 46a and a second intermediate layer 46b. Interior layer 42 is bonded to first intermediate layer 46a in the same manner as interior layer 42 is bonded to intermediate layer 46 in thermal pads 24 and 224. First intermediate layer 46a is bonded to second intermediate layer 46b in the same manner as intermediate layer 46 is bonded to exterior layer 44 of thermal pad 224. Thermal pad 324 differs from thermal pad 224 primarily in that exterior layer 44 of thermal pad 324 is positioned to encompass both intermediate layers 46a and 46b and to define a third fluid chamber 70 between exterior layer 44 and second intermediate layer 46b. Exterior layer 44 of thermal pad 324 is also stiffer than exterior layer 44 of thermal pads 24 and 224, in at least some embodiments.

Third fluid chamber 70 includes one or more ports (not shown) for coupling to one or more sources of positive or negative gauge fluid pressure. In some instances, third fluid chamber 70 is coupled via the port to negative gauge pressure (which may be supplied by thermal control unit 22 or another source) while second fluid chamber 56 is coupled to a supply of positive gauge pressure (which may also be supplied by thermal control unit 232 or another source). The negative gauge pressure in third fluid chamber 70, in combination with the relative stiffness of exterior layer 44, causes thermal pad 324 to be drawn inwardly toward the patient's skin, thereby ensuring close physical contact with, and better thermal transfer between, thermal pad 324 and the patient. The positive gauge pressure in second fluid chamber 56 supplies circulating air for controlling the microclimate between thermal pad 324 and the patient. As with the other thermal pads discussed herein, medicated vapors may be mixed with the source of positive gauge pressure gas supplied to second fluid chamber 56, and/or the humidity and/or temperature of this positive gauge pressure gas may be controlled by thermal control unit 22. First fluid chamber 52 receives the temperature controlled fluid from thermal control unit 22 that is used to control the temperature of the patient.

In some instances, positive gauge pressure may be applied to second fluid chamber 56 that has a high enough pressure to result in compressive forces being applied to the patient 30. In some instances, the application of compression to the patient using thermal pad 324 may be accomplished by applying negative gauge pressure to third fluid chamber 70 that is sufficient to draw or retain thermal pad 324 in close proximity to the patient. When so positioned, the expansion of second fluid chamber 56 due to its positive gauge pressure results in compressive forces being applied to the patient. Second and third fluid chambers 56 and 70 may also be used in other manners.

It will be understood that although second fluid chamber 56 has been described above as containing gas (positive or negative gauge pressure), alternative embodiments of one or more thermal pads can be constructed according to the present disclosure that use a liquid inside of second fluid chamber 56. Still further, although first fluid chamber 52 has been primarily described as being filled with a temperature controlled liquid supplied from thermal control unit 22, it will be understood that thermal control unit 22 can be modified to supply a temperature controlled gas that is supplied to first fluid chamber 52.

Still other modifications can be made. For example, in some embodiments, an ultraviolet light may be added that disinfects the fluid before being supplied to chambers 52 and/or 56, after exiting chambers 52 and/or 56, or while present in chambers 52 and/or 56. As another example, it is to be understood that the specific relative dimensions and positions of the chambers 52, 56, and/or 70 with respect to each other and/or with respect to top 32, bottom 34, and/or sides 36 may be changed from how they are shown in the accompanying drawings.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A thermal pad for controlling a patient's temperature, the thermal pad comprising:
   an interior layer adapted to be placed in contact with the patient;
   an intermediate layer sealed to a perimeter of the interior layer, the intermediate layer and interior layer being further secured together at a first set of internal locations within the perimeter of the intermediate layer;
   an exterior layer adapted to face away from the patient, the exterior layer sealed to a perimeter of the intermediate layer and secured to the intermediate layer at a second set of internal locations within the perimeter of the intermediate layer, wherein the first set of internal locations includes a first subset of internal locations that are included within the second set of internal locations and a second subset of internal locations that are not included within the second set of internal locations;
   a first chamber defined between the interior layer and the intermediate layer, the first chamber adapted to circulate a temperature controlled fluid from a first inlet in fluid communication with the first chamber to a first outlet in fluid communication with the first chamber; and
   a second chamber defined between the intermediate layer and the exterior layer, the second chamber in fluid communication with a port and a plurality of first holes defined in the interior layer at a plurality of internal locations included within the second subset.

2. The thermal pad of claim 1 wherein the plurality of first holes are defined at the first set of internal locations.

3. The thermal pad of claim 2 wherein the intermediate layer and the interior layer are secured together at the first set of internal locations by welds.

4. The thermal pad of claim 3 wherein the plurality of first holes are defined in a plurality of the welds.

5. The thermal pad of claim 1 wherein the plurality of first holes are distributed with sufficient density over the interior layer such that when negative gauge pressure is applied to the port, suction is created between the interior layer and the patient, thereby urging the thermal pad to retain contact with the patient.

6. The thermal pad of claim 1 wherein the plurality of first holes define first openings that pass through the interior and intermediate layers but not the exterior layer.

7. The thermal pad of claim 6 further comprising a plurality of second holes, the plurality of second holes defining second openings that pass through the interior layer, the intermediate layer, and the exterior layer.

8. The thermal pad of claim 7 wherein the first chamber is a liquid chamber and the second chamber is a gas chamber.

9. The thermal pad of claim 8 wherein the plurality of second holes are adapted to allow gas inside of said second chamber to be vented to ambient surroundings.

10. The thermal pad of claim 9 wherein pressurized gas delivered to the port in the second chamber flows through the plurality of first holes and onto the patient.

11. The thermal pad of claim 8 wherein negative gauge pressure applied to the port in the second chamber causes ambient air to enter the second chamber through the plurality of second holes.

12. The thermal pad of claim 1 further comprising a second exterior layer sealed to a perimeter of the exterior layer, the second exterior layer being not sealed to the exterior layer at any of the first set of internal locations or any of the second set of internal locations.

13. The thermal pad of claim 12 further comprising:
    a third chamber defined between the second exterior layer and the exterior layer.

14. The thermal pad of claim 13 wherein the third chamber is adapted to urge the interior layer toward the patient when subjected to a negative gauge pressure.

15. The thermal pad of claim 13 wherein the third chamber is adapted to intermittently urge the interior layer toward the patient when subjected to intermittent negative pressure to help counteract deep vein thrombosis in the patient.

16. The thermal pad of claim 12 wherein the plurality of first holes define first openings that pass through the interior and intermediate layers but not the exterior layer.

17. The thermal pad of claim 16 further comprising a plurality of second holes, the plurality of second holes defining second openings that pass through the interior layer, the intermediate layer, and the exterior layer, but not the second exterior layer.

18. A thermal pad for controlling a patient's temperature, the thermal pad comprising:
    an interior layer adapted to be placed in contact with the patient,
    an exterior layer adapted to face away from the patient, the interior and exterior layers being made of a flexible material adapted to be wrapped around a portion of the patient;
    a liquid chamber defined between the interior layer and the exterior layer, the liquid chamber adapted to circulate a temperature controlled fluid from a first inlet in fluid communication with the liquid chamber to a first outlet in fluid communication with the liquid chamber; and
    a first gas chamber defined between the interior layer and the exterior layer;
    a second gas chamber defined between the interior layer and the first gas chamber;
    a plurality of holes defined in the interior layer and in fluid communication with the second gas chamber such that air supplied from the second gas chamber that flows through the plurality of holes is able to control a microclimate defined between the thermal pad and the patient; and
    a resilient material positioned within the first gas chamber, wherein the first gas chamber is adapted to maintain a negative gauge pressure while the thermal pad is wrapped around a portion of the patient's body and to subsequently allow ambient air to enter into the first gas chamber after the thermal pad has been wrapped around the portion of the patient's body, and wherein the resilient material is adapted to be compressed when the negative gauge pressure is maintained, and to expand toward the portion of the patient's body when the negative gauge pressure is terminated such that the liquid chamber is urged into closer contact with the patient when the negative gauge pressure is terminated.

19. The thermal pad of claim 18 wherein the liquid chamber is fluidly isolated from the first gas chamber and the second gas chamber.

20. The thermal pad of claim 19 further including a cap and a threaded port in fluid communication with the first gas chamber, the threaded port adapted to create a hermetic seal for the first gas chamber when the cap is secured to the threaded port.

* * * * *